US012605544B2

(12) United States Patent
Yoshida et al.

(10) Patent No.:  US 12,605,544 B2
(45) Date of Patent:  Apr. 21, 2026

(54) ELECTROSTIMULATION DEVICE

(71) Applicant: ITO CO., LTD., Tokyo (JP)

(72) Inventors: Daigo Yoshida, Tokyo (JP); Ryoichi Takasu, Tokyo (JP); Wataru Orito, Tokyo (JP); Osamu Ito, Tokyo (JP); Hideki Arai, Tokyo (JP)

(73) Assignee: ITO CO., LTD., Tokyo (JP)

( * ) Notice: Subject to any disclaimer, the term of this patent is extended or adjusted under 35 U.S.C. 154(b) by 287 days.

(21) Appl. No.: 18/546,614

(22) PCT Filed: Feb. 16, 2022

(86) PCT No.: PCT/JP2022/006050
§ 371 (c)(1),
(2) Date: Aug. 16, 2023

(87) PCT Pub. No.: WO2022/176876
PCT Pub. Date: Aug. 25, 2022

(65) Prior Publication Data
US 2024/0123229 A1      Apr. 18, 2024

(30) Foreign Application Priority Data
Feb. 18, 2021     (JP) ................................. 2021-024704

(51) Int. Cl.
*A61N 1/36*          (2006.01)
*A61N 1/04*          (2006.01)
*A61N 1/32*          (2006.01)
(52) U.S. Cl.
CPC ....... *A61N 1/36034* (2017.08); *A61N 1/0452* (2013.01); *A61N 1/328* (2013.01)
(58) Field of Classification Search
None
See application file for complete search history.

(56) References Cited

U.S. PATENT DOCUMENTS

2009/0105795 A1*  4/2009  Minogue ................ A61N 1/321
                                                            607/148
2015/0328467 A1*  11/2015  Demers .............. A61N 1/37217
                                                            607/45
(Continued)

FOREIGN PATENT DOCUMENTS

JP        H08-112362 A      5/1996
JP        2000-014802 A     1/2000
(Continued)

OTHER PUBLICATIONS

European Patent Office, European (EP) Search Report issued in EP patent application No. 22756194.1, Munich Germany, 6 pages.

*Primary Examiner* — Michael W Kahelin
(74) *Attorney, Agent, or Firm* — ASLAN LAW, P.C.

(57)          ABSTRACT

Provided is an electrostimulation device that outputs an electrical signal, the electrical signal obtained by repeatedly outputting a fifth electrical signal comprising a first electrical signal whose amplitude in a first time becomes larger from a first amplitude, a second electrical signal whose amplitude in a second time is maintained to a second amplitude, a third electrical signal whose amplitude in a third time becomes smaller to a third amplitude, and a fourth electrical signal whose amplitude in a fourth time is maintained to a fourth amplitude; and the first electrical signal output in a sixth time, that is obtained by repeatedly outputting an eighth electrical signal comprising a sixth electrical signal having a first frequency, the sixth electrical signal that is off in a seventh time, wherein the first frequency is controlled via first frequency control of changing from a second frequency to a third frequency.

2 Claims, 10 Drawing Sheets

(56)        References Cited

U.S. PATENT DOCUMENTS

| 2018/0161233 A1 | 6/2018 | Nakanishi |
| 2022/0184395 A1 | 6/2022 | Yoshida et al. |

FOREIGN PATENT DOCUMENTS

| JP | 2010-75401 A | 4/2010 |
| WO | WO 2010035600 A1 | 4/2010 |
| WO | WO 2017/038822 | 9/2017 |
| WO | 2020/175650 A1 | 9/2020 |

* cited by examiner

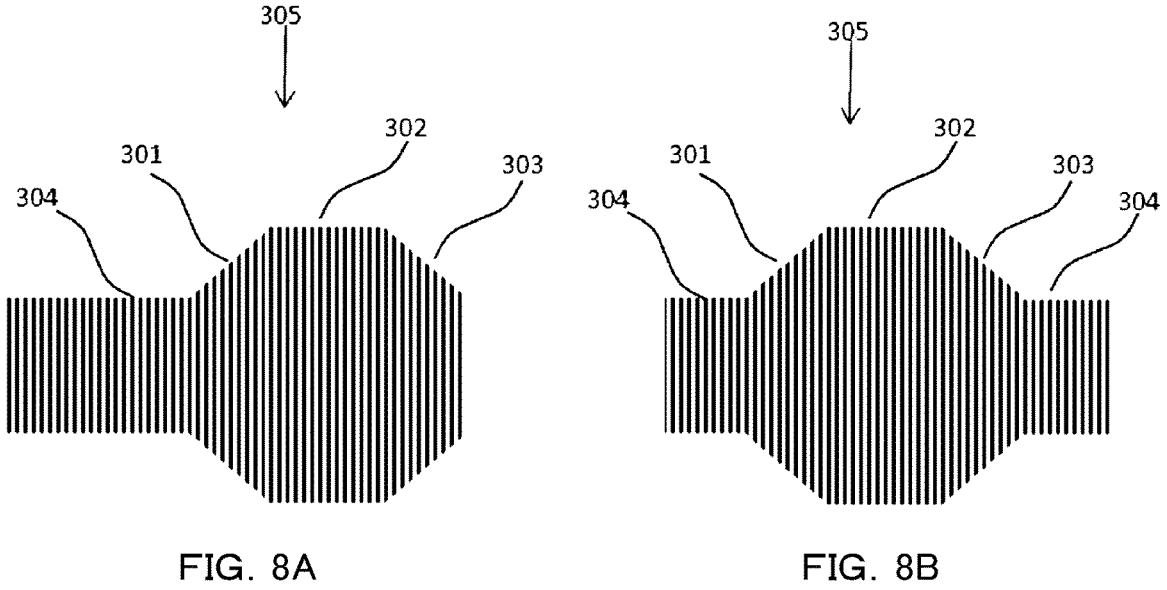
FIG. 8A                          FIG. 8B
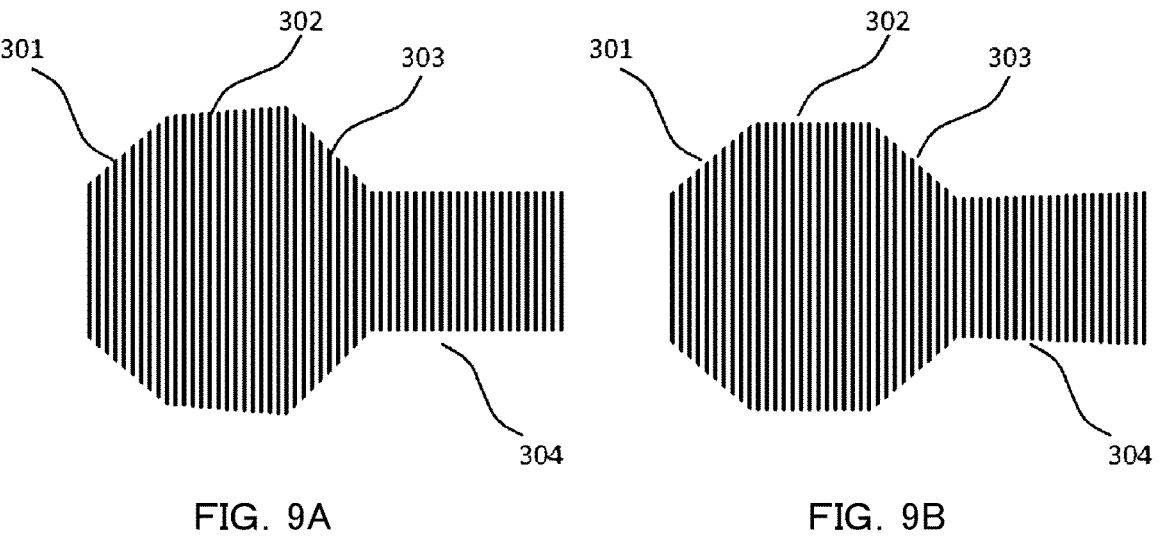
FIG. 9A                          FIG. 9B

ELECTROSTIMULATION DEVICE

TECHNICAL FIELD

The present invention relates to an electrostimulation device that feeds an electrical signal as a current supplied to an affected part and an examination region or an operation region on the occasion of treatment, rehabilitation, examination, massage or cosmetic treatment; and to a conductor used for the foregoing stimulator.

BACKGROUND ART

So-called physical therapy of performing treatment, massage, diagnosis or cosmetic treatment by applying physical energy to a part necessary for a patience or the like from outside, such as treatment using electromagnetic waves such as ultrashort waves and microwaves, treatment using a low or high frequency, potential treatment, treatment with a weak current or treatment with ultrasonic waves is worthy of attention; and many devices for realizing the foregoing, such as a medical treatment device, a diagnosis device, a training device and a cosmetic treatment device have been put into practical use. In the present specification, physical energies used for treatment and cosmetic therapy or diagnosis, for example, current and voltage or electric power having an AC component of a low frequency, a high frequency or the like, or a frequent component are collectively called; or each of them is called a pulse. Alternatively, it is also referred to as treatment waves, electrical stimulation, or an electrical signal. Further, the electrical signal may be a pulse train made from rectangular pulses and square pulses or stepwise pulses, or may be a pulse train made from a composite pulse; and it may be sine waves, triangle waves, saw-tooth waves, or an impulse train. Further, a synthetic wave and an interference wave each produced by interactions of a plurality of pulses are also referred to as a pulse or a synthetic pulse, and a synthetic wave produced from a sine wave is referred to simply as a pulse or a synthetic pulse.

Thereafter, in the present specification, a treatment device for applying electrical stimulation thereto, a medical device, a massage device, a diagnosis device and a cosmetic treatment device are collectively called an electrostimulation device. Treatment and diagnosis for which the electrostimulation device is used, massage, and an operation with a cosmetic therapy device for applying electrical stimulation thereto each are called therapy, or all of them are collectively called therapy. A curer and a massager using electrostimulation devices, a diagnostician using an electrostimulation device, and a cosmetic therapy operator and a trainer using the electrostimulation devices are called users, and those undergoing treatment are called patients. Further, a human body portion subjected to treatment given by electrical stimulation is called an affected part. Accordingly, unless otherwise clarified, the description of an electrostimulation device, that should not exclude a massage device, a diagnosis device and a cosmetic therapy device is not limited only to those having an injury or a disease even if being described as a patient, but includes those undergoing examination as well as a cosmetic therapy operation in addition to those undergoing massage or operations of fatigue recovery and injury prevention. Similarly, it is not limited only to an injury or disease region even if being described as an affected part, but shows a part of the body to be examined, or a part of the body subjected to a cosmetic therapy operation in addition to regions that undergo massage or operations of fatigue recovery and injury prevention.

Accordingly, unless otherwise clarified, pulses used for treatment should not exclude pulses used for massage, diagnosis or cosmetic therapy.

Nowadays, according to the electrostimulation device, an electrostimulation device that performs treatment by using and arranging a plurality of electrodes so as to sandwich an affected part, and supplying an electrical signal of a different frequency to the affected part from each electrode pair to generate interference waves inside the body is put into practical use. The treatment using the interference waves has the advantage of being able to perform effective treatment, even when the affected part is located at a deep portion from the body surface.

PRIOR ART DOCUMENT

Patent Document

Patent Document 1: Unexamined Japanese Patent Application Publication No. Hei 08-112362
Patent Document 2: PCT International Publication No. WO 2017/038822

SUMMARY OF THE INVENTION

Problems to be Solved by the Invention

The electrical signal supplied to an affected part reaches a deeper part when its frequency becomes larger. According to a technique as described in the above-described Patent Document 1, the reaching depth (hereinafter, referred to as an arrival depth) of electrical stimulation can be changed by changing the frequency. However, when only the same pulses are continuously used for the affected part, the affected part becomes difficult to react to the pulses, and thus the treatment effect tends to decrease. Then, the treatment effect can be prevented from decreasing by changing the frequency of pulses to be used. However, when using two pulses, in such a configuration in which only one out of the electrical signals of two frequencies to be used is changed, the other one is set to a fixed frequency, and thus there is a problem in which the effect of preventing the treatment efficiency from decreasing is not sufficient. Further, the purpose of treatment is diversified in relief of pain and muscular tension and so forth in addition to, for example, recovery of damaged muscle tissues simply caused by injuries or the like. However, these treatments generally produce only one effect at a time, and thus it needs to be treated one by one in order by applying pulses thereto at each fixed time in order to obtain a plurality of effects and the treatment takes time, thereby not increasing the treatment efficiency. Further, it is complicated to use a number of electrodes for using a plurality of pulses, for examples conductors. Further, as described in the above-described Patent Document 2, a method of using a suction cup as a method of using an electrode is put into practical use, but the suction cup is not always appropriate when using a lubricant such as gel, oil or the like. It is an objective to provide an electrostimulation device exhibiting high treatment efficiency to solve the foregoing problems with the present invention.

Means to Solve the Problems (1) In order to achieve the solution of problems, the present invention employs the following means. That is, it is a feature that the electrostimulation device is an electrostimulation device that outputs an electrical signal, the electrical signal obtained by repeatedly outputting a fifth electrical signal comprising a first electrical signal whose amplitude in a first time becomes larger from a first amplitude that is non-zero, a second electrical signal whose amplitude in a second time is maintained to a second amplitude that is non-zero, a third electrical signal whose amplitude in a third time becomes smaller to a third amplitude that is non-zero, and a fourth electrical signal whose amplitude in a fourth time is maintained to a fourth amplitude that is non-zero; and the first electrical signal output in a sixth time, that is obtained by repeatedly outputting an eighth electrical signal comprising a sixth electrical signal having a first frequency, the sixth electrical signal that is off in a seventh time, wherein the first frequency is controlled via first frequency control of changing from a second frequency to a third frequency.

(2) Further, it is a feature that in the electrostimulation device according to the present invention, the sixth electrical signal is controlled via the first frequency control, or second frequency control of being controlled from a fourth frequency to a fifth frequency.

Effect of the Invention

The present invention can provide an electrostimulation device capable of maintaining high treatment efficiency, and of providing an efficient treatment.

BRIEF DESCRIPTION OF THE DRAWINGS

FIG. 8(A) and FIG. 8(B) are an explanatory diagram explaining electrical signals used in an electrostimulation device according to the present invention.

FIG. 9(A) and FIG. 9(B) are an explanatory diagram explaining electrical signals used in an electrostimulation device according to the present invention.

DETAILED DESCRIPTION OF EMBODIMENTS

Figure 1:
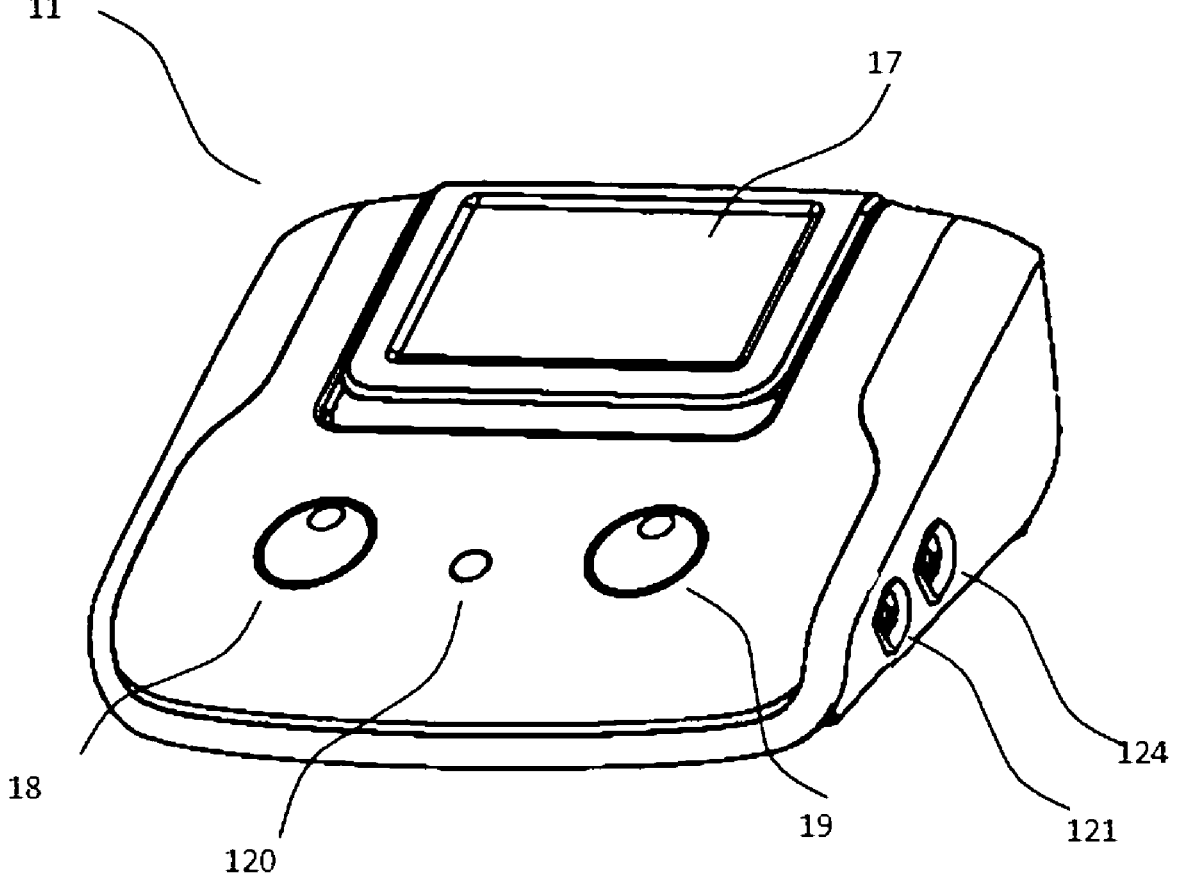
FIG. 1 is an explanatory diagram explaining a body part of an electrostimulation device according to the present invention.

FIG. 1 is a perspective view showing a body part 11 of an electrostimulation device 1 used for explaining the present invention according to the present embodiment. A controller 17, an encoder-A 18, an encoder-B 19, and a stop switch 120 together with a display section are provided on the front face of the body part 11 of the electrostimulation device 1; and a CH1 connector-R 121 for channel 1, and a CH2 connector-R 124 for channel 2 are provided on the right side face of the body part 11. A CH1 connector-L 122 for channel 1, and a CH2 connector-L 125 for channel 2 are provided on the left side face at positions corresponding to the right side face, but the right side face and the left side face each have an identical shape to each other, thereby omitting the descriptions. A main power supply 12 (not shown in the figure) is provided on the back face.

Figure 2:
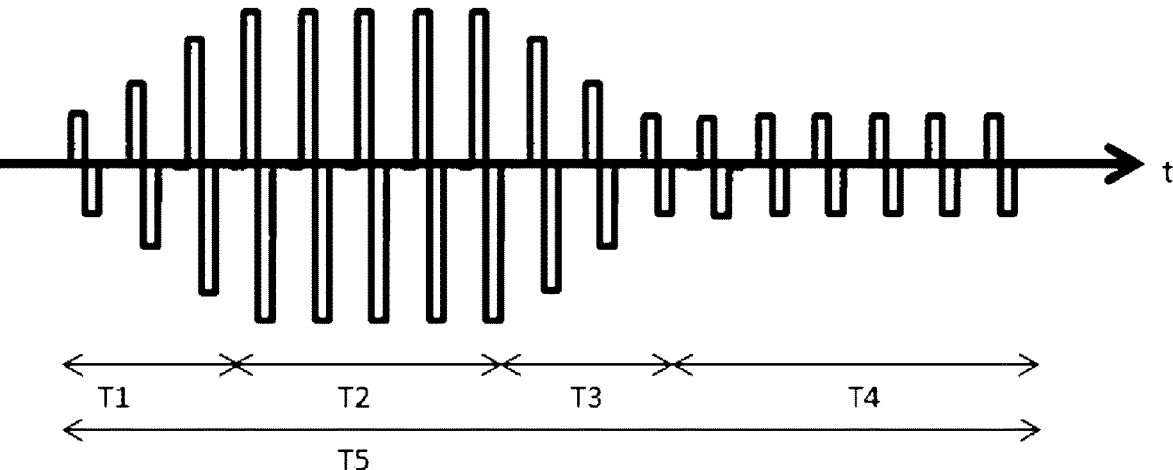
FIG. 2 is an explanatory diagram explaining electrical signals used in an electrostimulation device according to the present invention.

Next, the electrical signal output from the body part 11, that is supplied to an affected part is described. The electrical signal is supplied to the affected part by for example, adhesive electrode pad-A 111 and electrode pad-B 112 attached to the affected part. FIG. 2 schematically shows electrical signals supplied to a human body, for example, an affected part according to the present invention. The horizontal axis represents time, and the vertical axis represents amplitude, for example, the amplitude of a current value. When a pulse assembly is referred to as a pulse group, the electrical signal is constituted from a plurality of pulse groups. Specifically, the electrical signal in the present Example is given as a fifth electrical signal comprising a first electrical signal that is a pulse group whose amplitude becomes larger from a first amplitude as a non-zero amplitude, a second electrical signal that is a pulse group output continuously after the first electrical signal, whose amplitude is maintained as a non-zero amplitude, a third electrical signal that is a pulse group output continuously after the second electrical signal, whose amplitude becomes smaller to a third amplitude as a non-zero amplitude, and a fourth electrical signal whose amplitude as being non-zero is maintained to a fourth amplitude. The vertical axis is given as current values in FIG. 2, but the vertical axis may be given as voltage values or power values for electrical signals.

Figure 3:
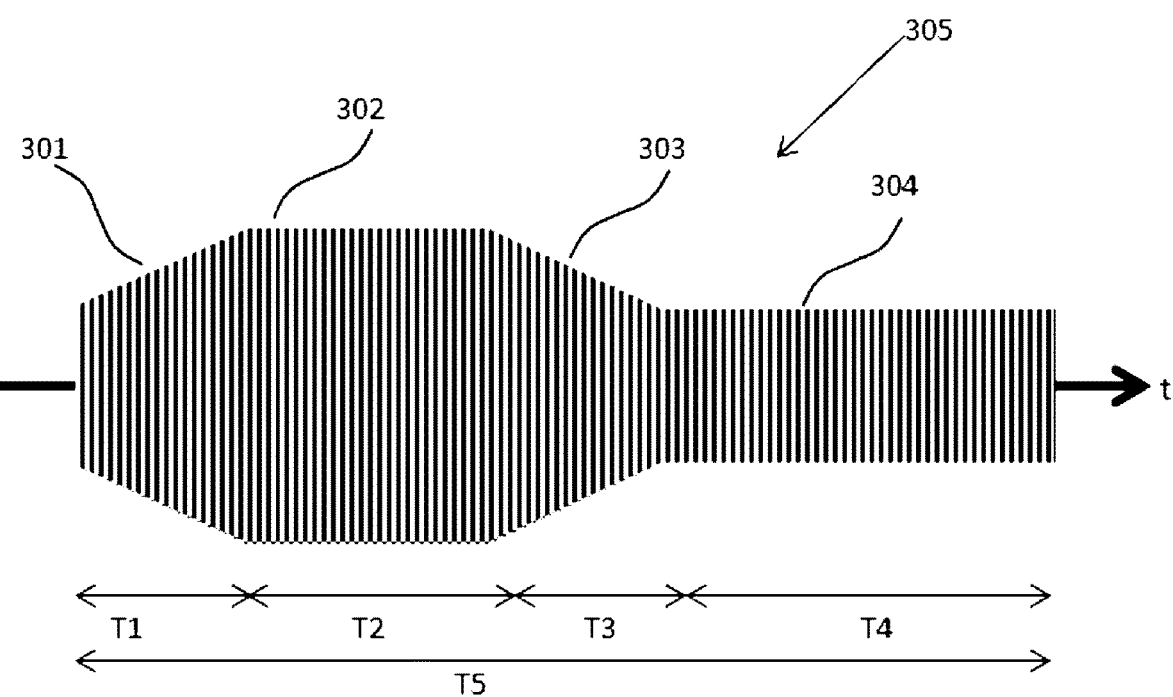
FIG. 3 is a cross-sectional view explaining electrical signals used in an electrostimulation device according to the present invention.

FIG. 3 schematically shows a fifth electrical signal, and for simplification, the schematic diagram in FIG. 3 is sometimes used for explanation as below. The first electrical signal, the second electrical signal, the third electrical signal, the fourth electrical signal and the fifth electrical signal are represented by a first electrical signal 301, a second electrical signal 302, a third electrical signal 303, a fourth electrical signal 304 and a fifth electrical signal 305, respectively; and respective duration times of the foregoing are represented by a first time T1, a second time T2, a third time T3, a fourth time T4 and a fifth time T5, as shown in FIG. 3.

Figure 4:
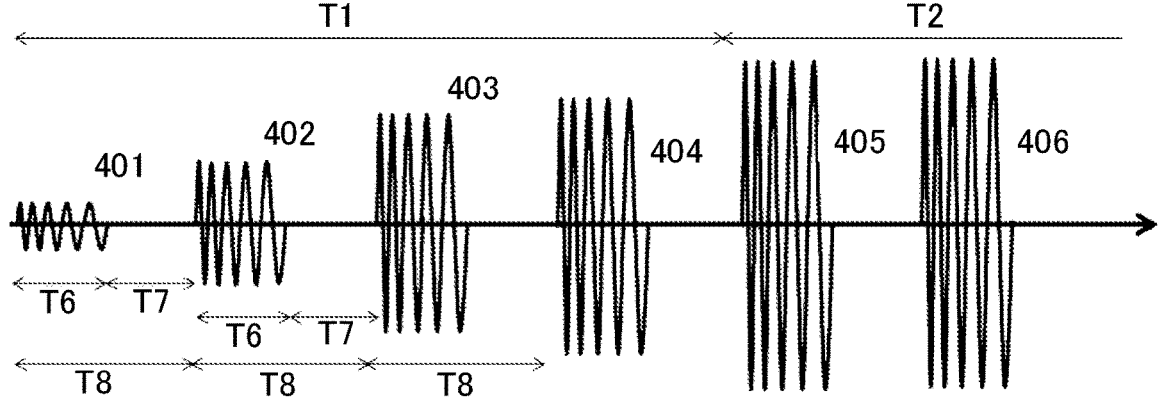
FIG. 4 is an explanatory diagram explaining electrical signals used in an electrostimulation device according to the present invention.

In addition, FIG. 2 schematically shows each electrical signal using only one period of rectangular wave pulses for simplification, but as schematically shown in FIG. 4, each electrical signal is practically constituted by ON/OFF of a plurality of sine waves. In FIG. 4, parts of head portions in the first time and the second time are schematically shown in enlarged forms. In the present embodiment, according to the first electrical signal, the sixth electrical signal of sine waves is output in the sixth time T6; the seventh electrical signal whose amplitude is smaller than that of the sixth electrical signal is output in the next seventh time T7 following the sixth time; and the eighth electrical signal comprising the sixth electrical signal and the seventh electrical signal in the eighth time T8 is repeatedly output. However, an example in which the amplitude of the seventh electrical signal is zero is described in the present embodiment, and time during which the output is substantially turned off is represented by T7. In addition, when using the seventh electrical signal, the frequency of the seventh electrical signal and the frequency of the sixth electrical signal may be identical to or different from each other.

In the present embodiment, the seventh time T7 is controlled so as to be identical to the sixth time T6. In other words, the eighth time T8 is considered as one period, and is controlled as a Duty of 50%. However, without being limited to the above-mentioned values, the seventh time and the sixth time each may be set to a different value therefrom. For example, the seventh time may be made to be shorter than the sixth time, or may be set to be oppositely longer than it.

According to the first electrical signal, the amplitude of the sixth electrical signal becomes gradually larger as shown in FIG. 4. Specifically in FIG. 4, the eighth electrical signal initially output in the first time T1 is represented by the eighth electrical signal-A 401; the eighth electrical signal output next to the eighth electrical signal-A 401 is represented by the eighth electrical signal-B 402; and the eighth electrical signal output next to the eighth electrical signal-B 402 is represented by the eighth electrical signal-C 403. Similarly to the above, in consideration of the eighth electrical signal-D 404, the eighth electrical signal-E 405 and the eighth electrical signal-F 406, that is, the four eighth electrical signals according to the first electrical signal, and the leading two eighth electrical signals according to the second electrical signal are schematically shown, but the figure becomes practically complicated, and thus they are schematically illustrated as shown in FIG. 4, though a number of the eighth electrical signals are present in, for example T1 so as to be determined by the first time T1 and the eighth time T8.

FIG. 4 shows a state where the amplitude of the sixth electrical signal is changed for every individual eighth electrical signal, but without being limited thereto, the control in such a manner that the amplitude in the first time finally becomes large may be allowed, though the amplitude of the sixth electrical signal becomes constant according to a plurality of the eighth electrical signals. For example, in the eighth electrical signal-A 401 and the eighth electrical signal-B 402, the amplitudes of the sixth electrical signals are identical to each other, but in the eighth electrical signal-C 403, the control in such a manner that the amplitude of the sixth electrical signal is changed may be allowed. In the eighth electrical signal-A 401 and the eighth electrical signal-B 402, the amplitudes of the sixth electrical signals are different from each other, but the control in such a manner that the amplitudes of the sixth electrical signals in the eighth electrical signal-C 403 and the eighth electrical signal-D 404 are identical to each other may be allowed. That is, the control in such a manner that the amplitudes of a plurality of the eighth electrical signals are changed for every plural sixth electrical signals in a stepwise manner may be allowed.

Further, in the eighth electrical signal, a case where the sixth electrical signal has its amplitude that becomes constant is exemplified and illustrated in FIG. 4, but the present invention is not limited thereto. That is, the control in such a manner that the amplitude becomes larger even in the eighth electrical signal (the sixth electrical signal) may be allowed. For the amplitude control in this case as well, the amplitude may be changed for every pulse, for example, for every one period of sine waves; and the control in such a manner that the amplitude is changed for every plural pulses, that is, for every plural periods of sine waves, that is, changed in one sixth electrical signal in a stepwise manner may be allowed.

Figure 5:
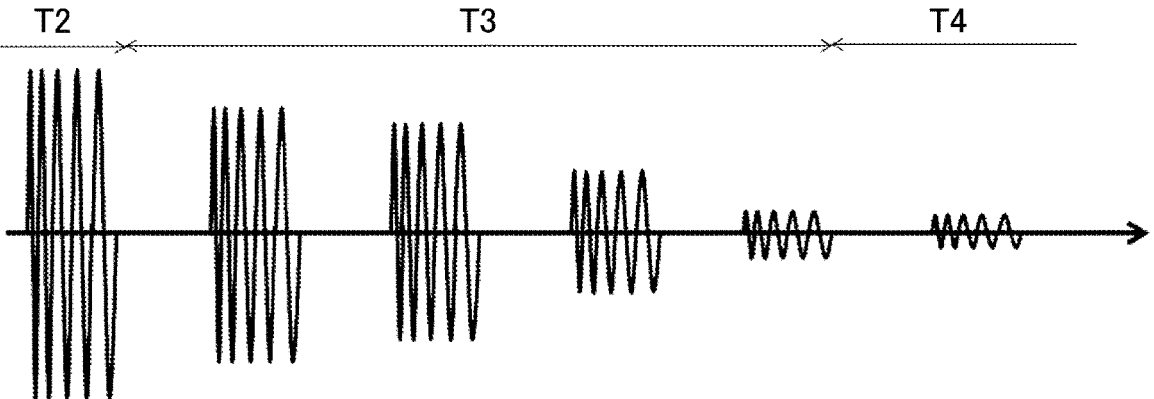
FIG. 5 is an explanatory diagram explaining electrical signals used in an electrostimulation device according to the present invention.

FIG. 5 is a schematic diagram showing part of the rear end of the second electrical signal, and front portions of the third electrical signal and the fourth electrical signal. For control concerning the amplitude for which FIG. 4 is used, the third electrical signal as well can be similarly applied. However, while the first electrical signal is controlled so as to have its amplitude that becomes larger, the third electrical signal is controlled so as to have its amplitude that becomes smaller, but a controlling way thereof is identical to that of the first electrical signal.

Figure 6:
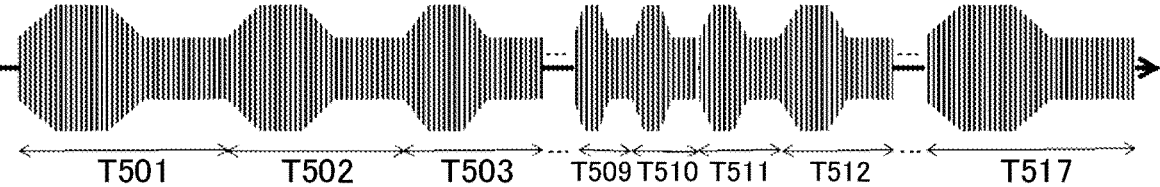
FIG. 6 is an explanatory diagram explaining electrical signals used in an electrostimulation device according to the present invention.

FIG. 6 shows a state where the fifth signal that is an electrical signal supplied to an affected part is repeatedly output in a different duration time therefrom. When the treatment begins, the fifth signal is output in T501, and the fifth electrical signals are subsequently output in T502, T503, . . . , respectively. The fifth signal has a duration time of one second in T501, of 0.67 seconds in T502, of 0.5 seconds in T503, of 0.4 seconds in T504, of 0.2 seconds in T509 so as to become shorter in a sequential manner. After that, of 0.22 seconds in T510, of 0.25 seconds in T511, of 0.29 seconds in T512, . . . so as to become longer in a sequential manner, and it is controlled so as to finally return to one second in T517. Thereafter, such a control is repeated. For example, T518 comes after T517, and the fifth signal in a time of 0.67 seconds is output. That is, a duration time from T501 to T517 during treatment time is repeated, and the fifth signal is output while gradually changing the duration time.

In FIG. 6, the first time T1, the second time T2, the third time T3 and the fourth time T4 are shown in the figure by exemplifying a case of being changed with a change of the fifth time T5, but the present invention is not limited thereto, and the control in such a manner that at least one of T3 and T4 is changed with a change of T5 may be allowed, though at least one of T1 and T3 is maintained to a fixed value. Alternatively, the control in such a manner that at least one of T1 to T4 is maintained to be fixed with respect to a change of T5 is allowed. Alternatively, the control in such a manner that at least one of T1 to T5 is changed with a change of T5 may be allowed.

The electrical signals described in FIG. 2 to FIG. 6 are able to deepen the arrival depth of the electrical signal and to give electrical stimulation to not only the body surface or its vicinity thereof but also a deep part by the sixth electrical signal and its turning on/off, or via further, repetition with the fifth electrical signal. Accordingly, since not only the effective treatment and operation are made possible, but a plurality of physical therapy methods as typified by pain relief, massage or cosmetic therapy operations are applied by one treatment, a plurality of effects can be obtained by one-time treatment. Effects of shortening a treatment duration, and so forth can be expected, and effective treatment can be efficiently carried out. Further, in the control as shown in FIG. 6, the duration time of the supplied electrical signal supplied is not fixed, thereby being always variably controlled; and patients feel as if the frequency of the supplied electrical signal is changed, and thus they hardly get used to the electrical stimulation, and excellent electrical stimulation effects continue over a long period of time, thereby being able to increase efficacy in treatment.

In the control as shown in FIG. 6, when T501 or the like is considered as one period, T501 becomes one second, and thus the frequency of the fifth signal in T501 becomes 1 Hz, and the fifth signal in T509 shows 0.2 seconds, and thus the frequency thereof becomes 5 Hz, thereby being controlled so as to end up being changed from a frequency of 1 Hz to a frequency of 5 Hz. However, without being limited thereto, the frequency may be controlled from 2 Hz, and be controlled to 10 Hz. Further, the control in FIG. 4 is the control in such a manner as to change at a constant change rate for every 0.5 Hz from 1 Hz to 5 Hz, but it may be allowed to be controlled for every 0.4 Hz or 0.6 Hz, for example, for every 1 Hz, that is, to be controlled with a fixed frequency change. FIG. 6 shows the control in which frequencies are changed to 5 Hz from 1 Hz and subsequently changed to 1 Hz from 5 Hz, and after this, the foregoing frequency control is repeated.

Herein, the sixth electrical signal is described. In FIG. 4 and FIG. 5, the first frequency as a frequency of sine waves and pulses that constitute the sixth electrical signal is controlled to 5 kHz as a third frequency thereof from 10 kHz as a second frequency thereof. That is, the first frequency is changed so as to become smaller. The present invention is not limited thereto, and not only the control in such a manner that the frequency is changed so as to become larger may be allowed, but also the control in such a manner that the frequency is changed so as to become larger and subsequently to become smaller may be allowed. Alternatively, the frequency may be controlled to become smaller and subsequently controlled to become larger. For example, when the second frequency is set to 5 kHz, and the third frequency is set to 10 kHz, it may be allowed to be controlled to 10 kHz from 5 kHz. Alternatively, the control in such a manner as to be controlled to 5 kHz from 10 kHz, and subsequently returned to 10 kHz may be allowed. In contrast, the control in such a manner as to be controlled to 10 kHz from 5 kHz and subsequently returned to 5 kHz may be allowed. That is, in the control concerning the sixth electrical signal, such a control completed with each sixth electrical signal may be repeated for every sixth electrical signal. In other words, one frequency control may be applied to each sixth electrical signal.

In the frequency control with respect to the sixth electrical signal, it may be allowed to be controlled so as to be completed using the one frequency control for a plurality of the sixth electrical signals, that is, to apply the first frequency control and the second frequency control to the sixth electrical signals different from each other; or the control in such a manner as to control the sixth electrical signal with the first frequency control or the second frequency control, or as to apply multiple frequency control to a plurality of the sixth electrical signals may be allowed.

Figure 7:
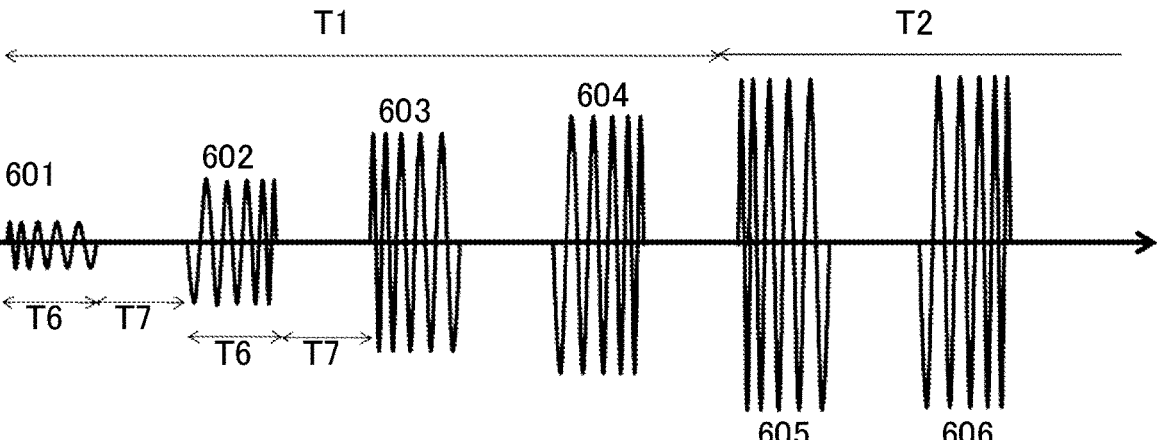
FIG. 7 is an explanatory diagram explaining electrical signals used in an electrostimulation device according to the present invention.

FIG. 7 shows one example. When taking the sixth electrical signal-A 601, the sixth electrical signal-B 602, the sixth electrical signal-C 603, the sixth electrical signal-D 604, the sixth electrical signal-E 605 and the sixth electrical signal-F 606 for the eighth electrical signal-A 401, the eighth electrical signal-B 402, the eighth electrical signal-C 403, the eighth electrical signal-D 404, the eighth electrical signal-E 405 and the eighth electrical signal-F 406, respectively, the frequency of the sixth electrical signal is controlled, for example, to the third frequency from the second frequency in the sixth electrical signal-A 601; and is controlled to the second frequency from the third frequency in the next sixth electrical signal-B 602. For example, when taking the second frequency and the third frequency for 10 kHz and 5 kHz, respectively, the sixth electrical signal-A 601 is controlled to a third frequency of 5 kHz from a second frequency of 10 kHz; and the next sixth electrical signal-B 602 is controlled to a second frequency of 10 kHz from a third frequency of 5 kHz.

According to the control as shown in FIG. 7, the frequency of the sixth electrical signal may be controlled to a third frequency of 5 kHz from a second frequency of 10 kHz as first frequency control thereof, and the frequency of the sixth electrical signal may be controlled to a fifth frequency of 10 kHz from a fourth frequency of 5 kHz as second frequency control thereof. The above-described control as shown in FIG. 7 shows a case where each of the third frequency and the fourth frequency that are identical to each other is 5 kHz, and each of the second frequency and the fifth frequency that are identical to each other is 10 kHz. However, the control according to the present invention is not limited thereto, and the control in which the third frequency and the fourth frequency are different from each other may be allowed, and the control in which the second frequency and the fourth frequency are different from each other may be allowed.

In FIG. 7, two sixth electrical signals are used to control frequencies, that is, to apply the first frequency control and the second frequency control to different sixth electrical signals from each other, but without being limited thereto, three or more frequency controls may be applied to a plurality of the sixth electrical signals. For example, the first frequency control, the second frequency control, and the third frequency control may be frequency controls so as to be controlled to a third frequency of 8 kHz from a second frequency of 10 kHz, to be controlled to a fifth frequency of 7 kHz from a fourth frequency of 8 kHz, and to be controlled to a seventh frequency of 10 kHz from a sixth frequency of 7 kHz, respectively.

The FIG. 8 shows other examples of the fifth electrical signal according to the present invention. It is described in FIG. 3 that the first electrical signal, the second electrical signal, the third electrical signal and the fourth electrical signal are output in this order to constitute the fifth electrical signal, but without being limited thereto, for example, as shown in FIG. 8(A), it may be allowed that the fourth electrical signal, the first electrical signal, the second electrical signal and the third electrical signal are output in this order to constitute the fifth electrical signal. Alternatively, as shown in FIG. 8(B), it may be allowed that after outputting the fourth electrical signal, the first electrical signal, the second electrical signal and the third electrical signal in this order, the fourth electrical signal is output again to constitute the fifth electrical signal.

The FIG. 9 shows other examples of the fifth electrical signal according to the present invention. As a state where the amplitude is maintained as with the second electrical signal and the fourth electrical signal, each example as described above shows the control in such a manner that the amplitude of the basic pulse is not changed, but without being limited thereto, it may be allowed to control the amplitude of the basic pulse in such a manner that the amplitude neither falls below a fixed value, nor exceeds it. FIG. 9(A) shows the control in such a manner that the amplitude of the second electrical signal does not become constant, and FIG. 9(B) shows a case where the fourth electrical signal is not constant. These may be controlled in such a manner that effects of the high-frequency electrical signal and the low-frequency electrical signal are appropriately obtained. The controls as shown in FIG. 9(A) and FIG. 9(B) are not alternative, and thus the control in such a manner that both the amplitudes of the second electrical signal and the fourth electrical signal do not become constant may be carried out. Further, these controls may also be applied to the fifth electrical signal as shown in FIG. 8.

Figure 10:
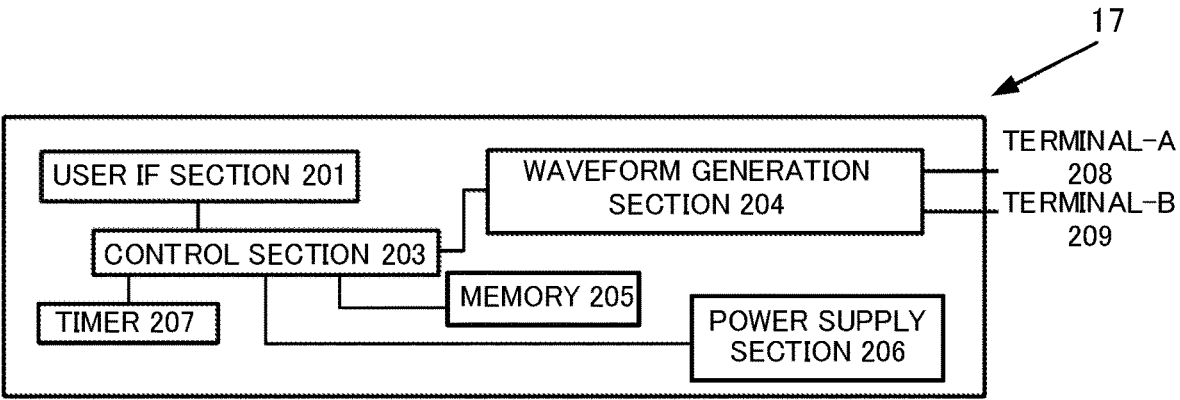
FIG. 10 is an explanatory diagram explaining a controller of an electrostimulation device according to the present invention.

FIG. 10 shows a block diagram of a controller 17. The controller 17 arranged inside a body part 11 controls an operation of the body part 11. The controller 17 is constituted from a waveform generation section 204 as an output circuit for outputting an electrical signal, a control section 203 that controls the waveform generation section 204, a timer 207, a user IF section 201, a power supply section 206, a memory 205, and so forth. The control section 203 in which an interface section connected with each section as described above is installed in addition to CPU and an internal memory is connected to the waveform generation section 204 that generates the electrical signal for providing current stimulation, the timer 207 for managing an output time, the user IF section 201 connected to the controller 17, and the memory 205 to control the aforementioned. Electric power consumed at each section is controlled to a predetermined fixed voltage value by the power supply section 206, and is supplied to each section via the control section 203.

The electrostimulation device 1 is used as followed. After a user first attaches the electrode pad-A 111 and the electrode pad-B 112 onto an affected part, the main power supply 12 is turned on. When the main power supply 12 is turned on, a state of the body part 11, and buttons as interfaces for various settings are displayed, for example, the buttons for selecting or setting a treatment mode and an output level are displayed on the controller 17. The controller 17 is, for example a touch panel type liquid crystal display, thereby serving as display means and input means. When tapping the display at a displayed output level, an encoder-A 18 is enabled, and thus the amplitude as an output of the aftermentioned electrical signal can be set by rotating the encoder-A 18. The encoder-A 18 is used for channel 1, and the encoder-B 19 is used for channel 2. Further, when the user selects the treatment mode using the controller 17, each parameter of an electrical signal used in the selected treatment mode is read from the memory 205, and is supplied to the waveform generation section 204; information thereof is subsequently sent to the control section 203 via the user IF section 201, when the user presses a switch displayed on the controller 17; and the control section 203 gives instructions to the waveform generation section 204 so as to output the above-described electrical signal. The waveform generation section 204 outputs an electrical signal in accordance with the supplied parameter, and the output electrical signal is supplied to an affected part by the electrode pad-A 111 via a cord 16 connected to a terminal-A 208, and the electrode pad-B 112 via a cord 16 connected to a terminal-B 209. The terminal-A 208 and the terminal-B 209 are applicable to the channel 1, but outputting to the channel 2 is performed by other terminals arranged at the waveform generation section 204. Information whose electrical signal is simultaneously output is sent to the timer 207, and the timer 207 starts clocking of time during which the electrical signal is output by the waveform generation section 204 as being time, for example treatment time, that is of time during which the electrical signal is supplied to the affected part, for example, of 20 minutes. Information about measurement of the timer 207, for example, information about lapse of time is fed back to the control section 203, and the control section 203 stops electric power supplied to the waveform generation section 204 via feed-back thereof to stop outputting of the electrical signal. The treatment time as being not limited to 20 minutes may be not less than, and less than 20 minutes, and may be a configuration in such a manner that the user is appropriately settable or adjustable in consideration of a state of the affected part. In addition, the stop switch 120 is used to forcibly stop outputting of all the electrical signals in an unexpected situation.

Figure 11:
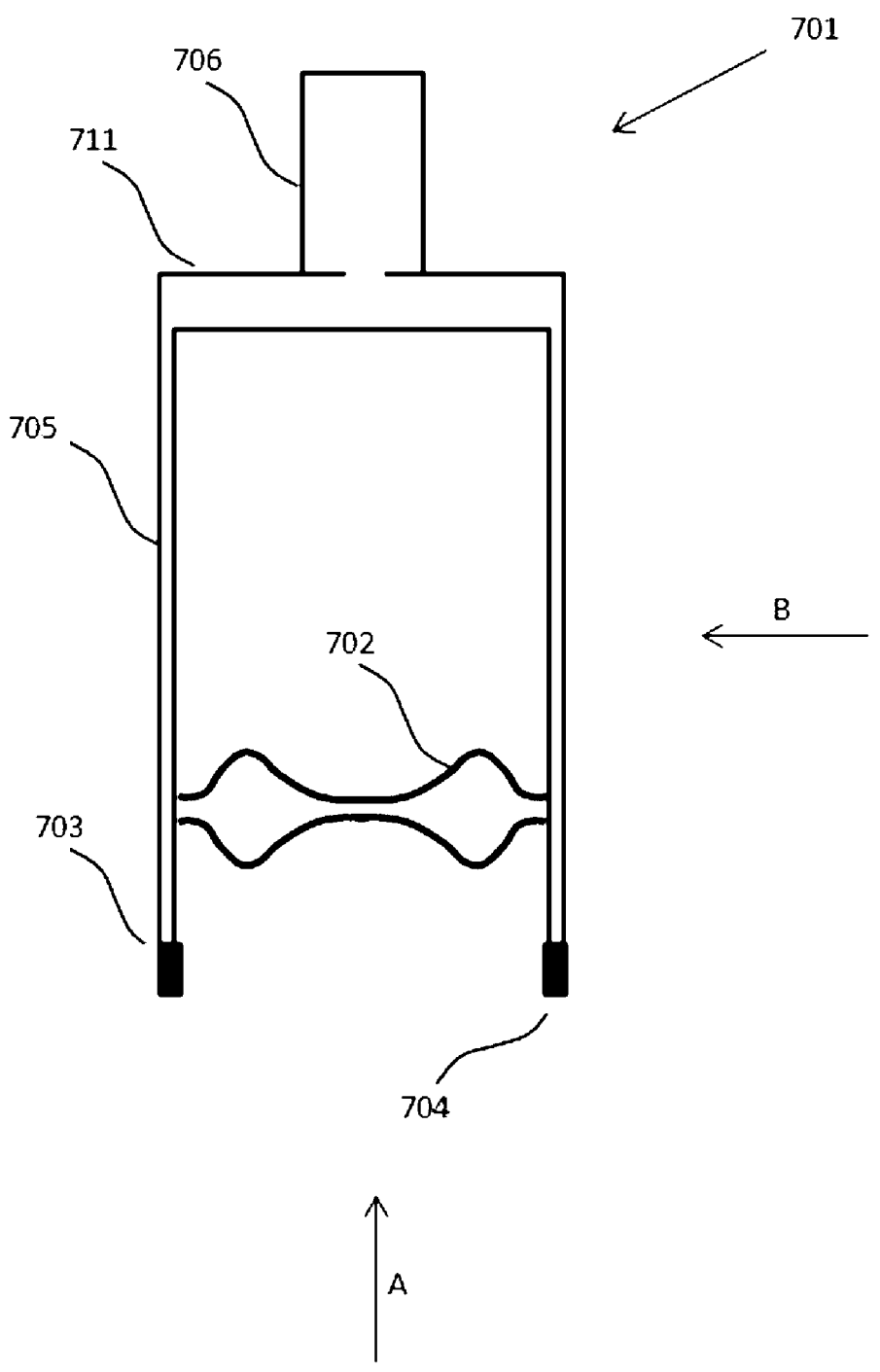
FIG. 11 is an explanatory diagram explaining a suction cup of an electrostimulation device according to the present invention.

In the above, the electrical signal is described by exemplifying a case where the electrode pad-A 111 and the electrode pad-B 112 that are attached onto an affected part or its periphery as adhesive pads are used, but according to the present invention, the suction cup-A 701 may be used as schematically shown in FIG. 11. FIG. 11 schematically shows a central cross-section including a rotational shaft of a roller 702 in the suction cup-A 701, and a center of a cylindrical cup 705, and the roller 702 is arranged inside the cylindrical cup 705 in a freely rotatable manner, as shown in the figure. An electrode section-A 703 and an electrode section-B 704 are arranged at a lower end of the cup 705. A connection section 706 is arranged to a top plate 711 at the upper portion of the cup 705, and a hose 707 is connected thereto. The hose 707 is connected to a suction pump to suck air inside the cup 705, and thus the inside of the cup 705 becomes a negative pressure, and the suction cup-A 701 is adsorbed to the affected part. A cable connected to the body part 11 is enclosed in the hose 707, and the electrical signal output from the body part 11 is supplied to the electrode section-A 703 and the electrode section-B 704 by a wiring pattern arranged inside the cup 705.

Figure 12:
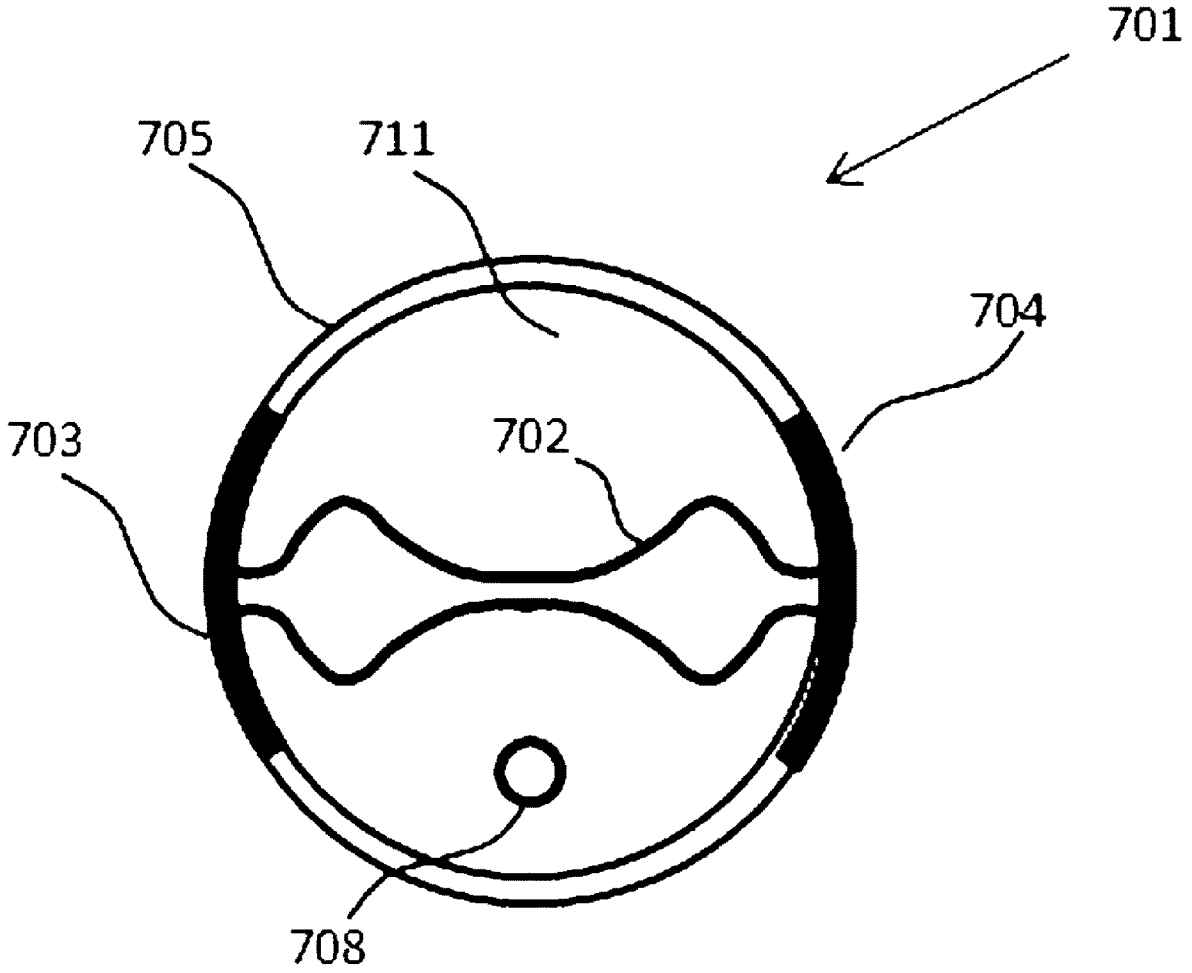
FIG. 12 is an explanatory diagram explaining a suction cup of an electrostimulation device according to the present invention.

FIG. 12 schematically shows the suction cup-A 701 as viewed from the arrow-A direction in FIG. 11. As shown in FIG. 12, an exhaust opening 708 for discharging air inside the cup 705 is arranged at the top plate 711 arranged at the upper portion of the cup 705. The exhaust opening 708 is not arranged right above the roller 702, that is, not obliquely arranged above the roller 702 when placing the suction cup-A 701 on a horizontal board, but obliquely arranged above the roller 702 at a position of being deviated from vertically above the roller 702.

Figure 13:
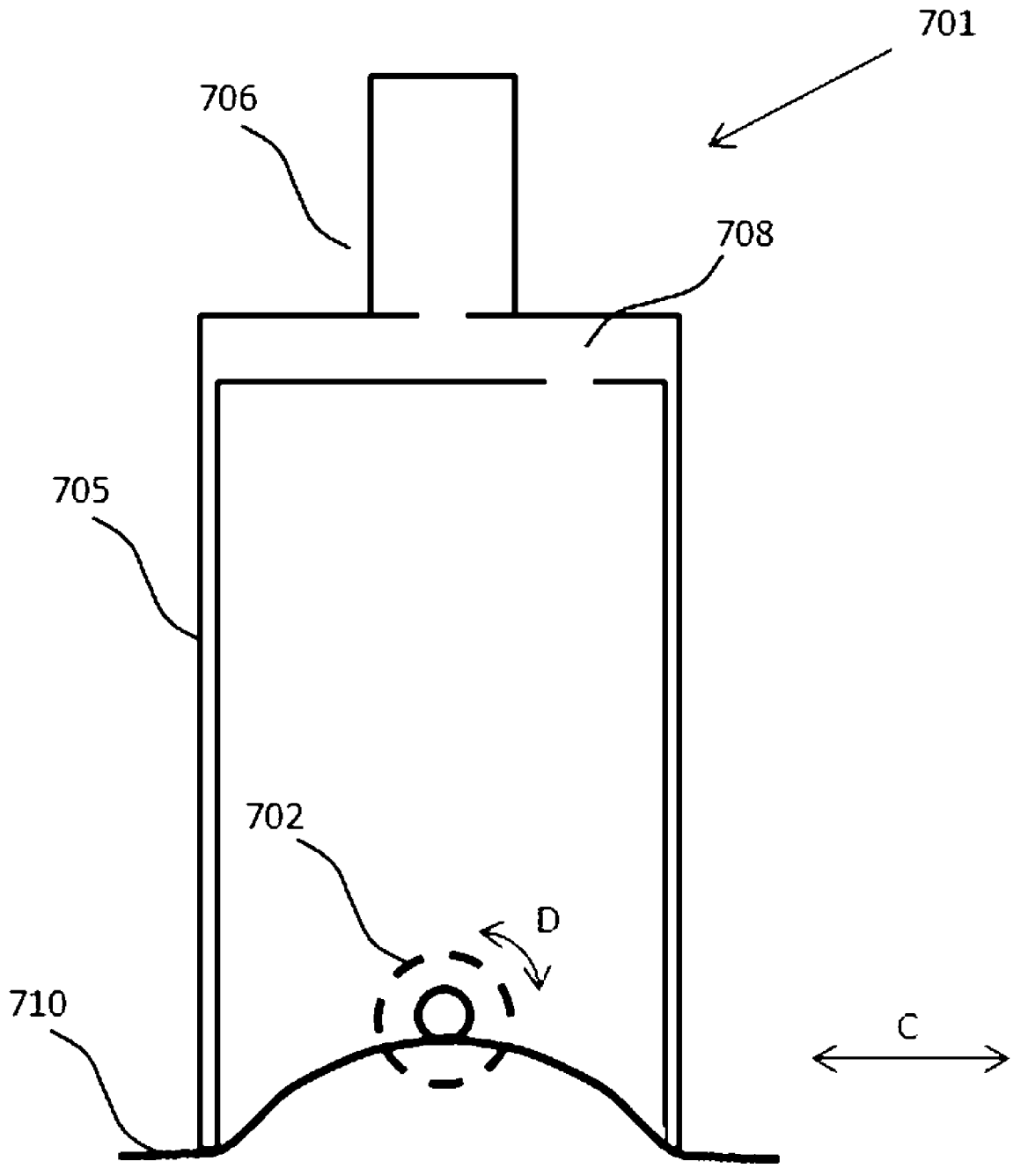
FIG. 13 is an explanatory diagram explaining a suction cup of an electrostimulation device according to the present invention.

FIG. 13 shows a schematic cross-section of the suction cup-A 701 as viewed from the arrow-B direction in FIG. 11. As shown in FIG. 13, the exhaust opening 708 is not arranged right above the roller 702, but arranged obliquely upward at the upper portion of the cup 705. The dotted line in the figure shows the portion where the roller 702 has a large diameter. The suction cup-A 701 is used while sucking the affected part 710 or its periphery, and moving a skin surface in the arrow-C direction in FIG. 13. The affected part 710 comes into contact with the roller 702 via suction as shown in FIG. 13, and further, the roller 702 is rotated in the arrow-D direction with movement of the suction cup-A 701.

A roller used for a conventional suction cup has a larger diameter of the central part thereof than that at the end, but the roller 702 is constituted in such a manner that the diameter at the central part is smaller than that at the end or its periphery.

A lubricant such as gel, oil or the like is often used and coated between the suction cup-A 701 and the affected part in order to make the suction cup-A 701 smooth. In a case where such a lubricant is used, it often remains inside the cup 705 when the suction cup-A 701 moves the skin surface. Specifically, in a case where the roller is arranged like the suction cup-A 701, there is caused a problem such that the lubricant remains at the upper portion of the roller, and thus the exhaust opening is clogged by sucking the remaining lubricant from the exhaust opening. Even when being assumingly discharged without clogging of the exhaust opening with the sucked lubricant, the lubricant discharged from the exhaust opening is sucked by the suction pump, thereby adversely affecting the suction pump, deteriorating performance of the suction pump, and shortening lifetime thereof, or failure is induced, and thus no device capable of providing highly reliable and excellent treatment for a long period of time can be realized.

Then, the configuration in which the lubricant is difficult to flow into the exhaust opening by keeping the roller surface away from the exhaust opening. In order to make the distance between the roller surface and the exhaust opening longer, it is effective that the diameter of a roller at the portion where the distance between the exhaust opening and the rotational shaft of the roller is short is made to be smaller than that at the other portion. In other words, a perpendicular line is drawn from the exhaust opening 708 to the rotational shaft of the roller 702, the diameter of the roller 702 at an intersection of the perpendicular line and the rotational shaft of the roller 702 or its periphery may be made to be smaller than the diameter at the other portion. As to the suction cup-A 701, as shown in FIG. 11, FIG. 12 and so forth, the diameter at the portion where the distance between the exhaust opening 708 and the rotational shaft of the roller 702 is short is made to be smaller than that at the other portion of the roller 702, and thus the lubricant remaining at the upper portion of the roller 702 inside the cup 705 is prevented from flowing into the exhaust opening 708 by making the distance between the exhaust opening 708 and the surface of the roller 702 longer, or prevented from being sucked into the exhaust opening 708. The lubricant in particular tends to remain at the central part of the roller, and thus the remaining lubricant tends to be sucked into the exhaust opening 708. Then, like the roller 702, the diameter at the central part is preferably made to be smaller than that at the end or its periphery; failure avoidance and longer life-time of the suction pump connected to the suction cup-A 701 can be achieved by preventing the lubricant from flowing into the exhaust opening 708, or being sucked thereinto; and as a result, the electrostimulation device capable of maintaining high treatment efficiency can be provided by avoiding labor loss, and time caused by maintenance or failure.

Further, in order to make the distance between the roller surface and the exhaust opening be longer, the position of the exhaust opening is not arranged right above the roller, but the exhaust opening is arranged so as to become obliquely above the roller, and possibility that the lubricant remaining inside the cup 705 flows into the exhaust opening 708 can be lowered by making the distance from the roller surface to the exhaust opening be longer. In other words, the exhaust opening 708 may be arranged at an edge of the top plate 711 or its periphery. Alternatively, the exhaust opening 708 may be arranged so as to become a position where the distance between the exhaust opening 708 and the roller 702 is not the shortest. In the suction cup-A 701, the exhaust opening 708 is not arranged right above or vertically above the roller 702, but arranged obliquely above the roller 702, that is, arranged so as to become an oblique position from vertically above, and in-flow of the lubricant to the exhaust opening 708 is made to be hardly generated by further making the distance from the surface of the roller 702 to the exhaust opening 708 be longer.

As a method of making the distance between the roller surface and the exhaust opening be longer, it may only be used that the roller diameter at the portion where the distance between the exhaust opening and the rotational shaft of the roller is short is made to be smaller than the diameter of the roller part at the other portion; and it may only be used that the position of the exhaust opening is not arranged right above the roller, but so as to be arranged obliquely above the roller. Alternatively, like the suction cup-A 701, both of them may be used. Alternatively, like the suction cup-A 701, the top plate 711 where the exhaust opening 708 is arranged is not made to be a flat surface, but it is also effective that the top plate comprises a recess recessed in the opposite direction of the roller, and the distance between the roller and the exhaust opening is made to be longer by providing the exhaust opening to the recess; and further, it is more preferably used at the same time to arrange the exhaust opening obliquely above the roller, and to make the roller diameter at the portion near the exhaust opening be smaller.

In addition, the above-described roller 702 has a configuration in such a manner that the diameter at the central part thereof becomes small, but without being limited thereto, for example, the configuration in such a manner that the diameter at only one of the ends thereof becomes small may be allowed. In this case, the exhaust opening may be provided above the portion where the diameter becomes small, and further, the exhaust opening is not arranged right above the portion where the diameter becomes small, but the exhaust opening may be arranged obliquely upward.

In the suction cup-A 701, the lubricant remaining inside the cup 705 is prevented from flowing into the exhaust opening 708 or being sucked thereinto, by shape of the roller 702 and the positional relationship between the roller 702 and the exhaust opening 708, but just in case, a filter through which the lubricant does not pass, but air passes may be arranged at the exhaust opening 708. The filter is clogged shortly when a large amount of the lubricant is sucked to the exhaust opening 708, when the lubricant frequently flows thereinto, or the like; and thus not much effect can be conventionally expected as measures by which no lubricant is made to flow into the exhaust opening 708. However, like the suction cup-A 701, in a case where it can be sufficiently limited by the shape of the roller 702 and the positional relationship thereof with the exhaust opening 708 that the lubricant flows into the exhaust opening 708, even when the lubricant flows into the exhaust opening 708 in an unexpected situation, a large amount of the lubricant does not flow into the exhaust opening 708 at once, and no clogging is shortly caused even if a filter is arranged, and thus the filter more preferably becomes sufficiently effective.

In the suction cup-A 701, the electrical signal output from the body part 11 is supplied to an affected part via the electrode section-A 703 and the electrode section-B 704. The using electrical signals may be electrical signals described referring to FIG. 2 to FIG. 9, or they may be high-frequency waves or radio waves of several kHz or higher. Alternatively, they may be low-frequency signals of several ten Hz, for example, pulses used for TENS (transcutaneous electrical nerve stimulation).

Figure 14:
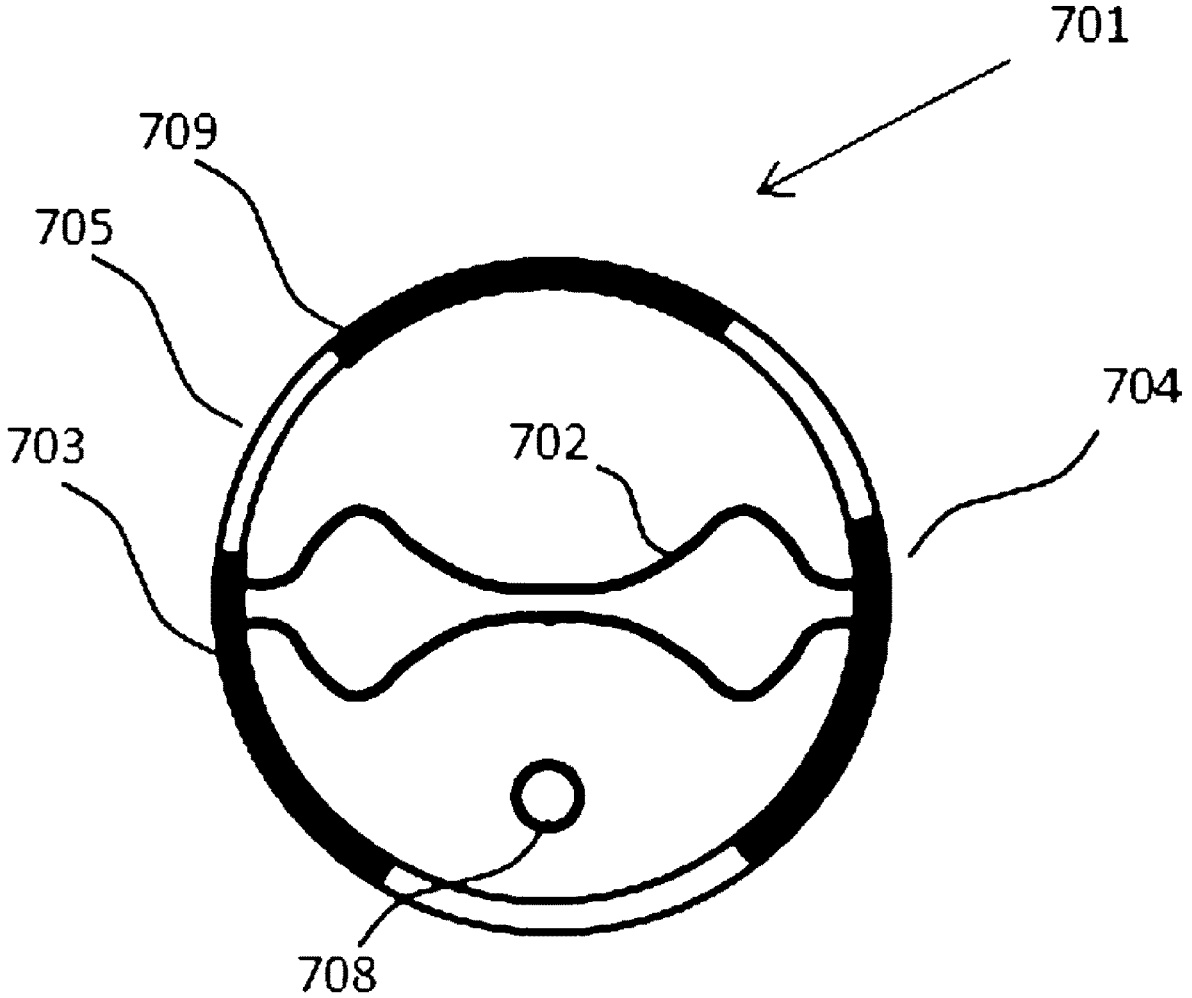
FIG. 14 is an explanatory diagram explaining a suction cup of an electrostimulation device according to the present invention.

The electrodes used in the suction cup-A 701 may be two electrodes as shown in FIG. 11, and an electrode section-C 709 may further be additionally provided therein as shown in FIG. 14. When a plurality of electrodes are arranged in such a manner, it may be so constituted that current flows only between specific electrodes, for example, the control in such a manner that an electrode flows not only between an electrode section-C 709 and an electrode section-A 703 but also between the electrode section-C 709 and an electrode section-B 704, but no current flows between the electrode section-A 703 and the electrode section-B 704 may be allowed. Alternatively, the control or the like in such a manner that the current flows not only between the electrode section-A 703 and the electrode section-C 709 but also between the electrode section-A 703 and the electrode section-B 704, but no current flow between the electrode section-C 709 and the electrode section-B 704 may be allowed.

Alternatively, for example, the current first flows between the electrode section-C 709 and the electrode section-A 703, followed by the current flowing between the electrode section-C 709 and the electrode section-B 704, and the current subsequently flows between the electrode section-A 703 and the electrode section-B 704; and the control or the like in such a manner that these are repeated may be allowed.

Alternatively, the current flows not only between the electrode section-A 703 and the electrode section-C 709 but also between the electrode section-A 703 and the electrode section-B 704, followed by the current flowing not only between the electrode section-B 704 and the electrode section-C 709 but also between the electrode section-A 703 and the electrode section-B 704, and further, the current subsequently flows not only between the electrode section-C 709 and the electrode section-A 703 but also between the electrode section-C 709 and the electrode section-B 704; the control or the like in such a manner that these are further repeated may be allowed.

In FIG. 12, the electrode section-A 703 and the electrode section-B 704 as two electrodes are arranged in such a manner that the current flowing via these two electrodes becomes parallel to the rotational shaft of the roller 702, but without being limited thereto, the electrodes may be arranged in such a manner that the current flows in a direction perpendicular to the rotational shaft of the roller 702

With regard to the suction cup-A 701, it is described as above that the suction pump is used in order to negatively pressurize the inside of the cup 705, but without being limited thereto, the configuration of using a blow-out type suction cup in place of the suction cup-A 701 may be allowed. The blow-out type suction cup is of a method of sucking air inside the cup 705 using the Bernoulli Principle by feeding air to the suction cup with a blow-out pump. The hose used for the suction pump needs to exhibit a certain level of strength so as to prevent the hose from being crushed or being bent due to a negative pressure inside the hose via suction, thereby highly tending to become a hard and heavy hose. On the other hand, when using the blow-out type suction cup, crushing or bending caused by the negative pressure inside the hose is prevented, and thus the using hose can be advantageously not only lightened but also softened. Further, air is not sucked but fed by a pump, and thus the lubricant does not reach the pump even if the lubricant flows into the exhaust opening 708, thereby not advantageously inducing deterioration or failure of the pump. On the other hand, a discharge port from which air fed to the suction cup and air inside the cup 705 are discharged needs to be arranged to the suction cup, and thus the discharge port is clogged when the lubricant sucked into the exhaust opening reaches the discharge port. Alternatively, the lubricant is often scattered to a patient from the discharge port, and thus the lubricant should be prevented from being sucked into the exhaust opening. Thus, even if being the blow-out type suction cup, it should be so constituted that the lubricant is prevented from flowing into the exhaust opening 708 or being sucked thereto due to cup 705 and the roller 702 as described above, or by using the above-described filter. In addition, it may be so constituted that the discharge port is arranged onto a wall face of the suction cup such as the cup 705, the connection section, or the like, that is, that the discharge port is arranged so as to be turned sideways while having a horizontal direction component; but the discharge port may be arranged so as to vertically face upward, for example, be arranged on the upper surface of the suction cup. A user can easily and visually confirm the discharge port by providing the discharge port so as to vertically face upward, for example, providing it on the upper surface portion of the suction cup, and thus even when the lubricant is attached to the discharge port just in case, the user notices that immediately and can perform cleaning; and efficient treatment of preventing suction force from being lowered due to clogging of the discharge port by avoiding clogging of the discharge port to prevent treatment efficiency from being lowered is made possible.

In addition, the present international application claims priority under Japanese Patent Application No. 2021-24704, filed Feb. 18, 2021, and the entire content of Japanese Patent Application No. 2021-24704 is applied to the present international application.

EXPLANATION OF THE SYMBOLS

11 Body part
12 Main power supply
16 Cord
17 Controller
18 Encoder-A
19 Encoder-B
111 Electrode pad-A
112 Electrode pad-B
120 Stop switch
121 CH1 connector-R
122 CH1 connector-L
124 CH2 connector-R
125 CH2 connector-L
201 User IF section
203 Control section
204 Waveform generation section
205 Memory
206 Power supply section
207 Timer
208 Terminal-A
209 Terminal-B
301 First electrical signal
302 Second electrical signal
303 Third electrical signal
304 Fourth electrical signal
305 Fifth electrical signal
401 Eighth electrical signal-A
402 Eighth electrical signal-B
403 Eighth electrical signal-C
404 Eighth electrical signal-D
405 Eighth electrical signal-E
406 Eighth electrical signal-F
601 Sixth electrical signal-A
602 Sixth electrical signal-B
603 Sixth electrical signal-C
604 Sixth electrical signal-D
605 Sixth electrical signal-E
606 Sixth electrical signal-F
701 Suction cup-A
702 Roller
703 Electrode section-A
704 Electrode section-B

705 Cup
706 Connection section
707 Hose
708 Exhaust opening
709 Electrode section-C
710 Affected part
711 Top plate

The invention claimed is:

1. An electrostimulation device that outputs an electrical signal comprising:

an electric signal generator configured and/or programmed to output the electric signal;

a control circuitry configured and/or programmed to control the electric signal generator;

a set of electrodes configured and/or programmed to provide the output electric signal; and a power supply section configured and/or programmed to supply electric power to the electric signal generator and the control circuitry, wherein the electric signal is a repetitive output of a fifth electric signal, the fifth electric signal including:

a first electrical signal having an amplitude that becomes larger from a first amplitude being non-zero, a second electrical signal having an amplitude that is maintained to a second amplitude being non-zero, a third electrical signal having an amplitude that becomes smaller to a third amplitude being non-zero, and a fourth electrical signal having an amplitude that is maintained to a fourth amplitude being non-zero, wherein each of the first electric signal, the second electric signal, the third electric signal and the fourth electric signal is a repeated alternating sequence of a pulse train, and said each of the first electric signal, the second electric signal, the third electric signal and the fourth electric signal having an off time where the pulse train is not outputted, and each pulse in each of the pulse trains is output at a first frequency value that is controlled by the control circuitry based on controlling the first frequency value, the first frequency value is swept between a second frequency a third frequency.

2. The electrostimulation device according to claim 1, wherein the first frequency control is performed in every pulse train by the control circuitry wherein the first frequency value is equal to the second frequency at the beginning of each pulse train, and the first frequency value changes until the first frequency value reaches the third frequency at the end of each pulse train.

* * * * *